US012788918B2

United States Patent
Schnell

(10) Patent No.: US 12,788,918 B2
(45) Date of Patent: Nov. 10, 2026

(54) TRACHEAL VENTILATION DEVICE HAVING OPTIMIZED CUFF TUBE

(71) Applicant: Coloplast A/S, Humlebaek (DK)

(72) Inventor: Ralf Schnell, Seligenstadt (DE)

(73) Assignee: Coloplast A/S, Humlebaek (DK)

( * ) Notice: Subject to any disclaimer, the term of this patent is extended or adjusted under 35 U.S.C. 154(b) by 948 days.

(21) Appl. No.: 17/907,841

(22) PCT Filed: Feb. 18, 2021

(86) PCT No.: PCT/EP2021/053948
§ 371 (c)(1),
(2) Date: Aug. 29, 2022

(87) PCT Pub. No.: WO2021/175602
PCT Pub. Date: Sep. 10, 2021

(65) Prior Publication Data

US 2023/0105430 A1 Apr. 6, 2023

(30) Foreign Application Priority Data

Mar. 2, 2020 (DE) ..................... 10 2020 105 522.6

(51) Int. Cl.
*A61M 16/04* (2006.01)
*A61M 16/00* (2006.01)

(52) U.S. Cl.
CPC . *A61M 16/0434* (2013.01); *A61M 2016/0027* (2013.01)

(58) Field of Classification Search
CPC .............. A61M 16/04; A61M 16/0402; A61M 16/0434; A61M 16/044; A61M 2016/0027; A61M 2205/3344; A61M 2205/7527; A61M 2025/1075
See application file for complete search history.

(56) References Cited

U.S. PATENT DOCUMENTS

| | | | | |
|---|---|---|---|---|
| 3,695,921 | A * | 10/1972 | Shepherd et al. | A61L 29/041 427/2.3 |
| 4,729,914 | A * | 3/1988 | Kliment | C08J 7/056 428/420 |
| 4,994,047 | A * | 2/1991 | Walker | A61L 29/06 600/581 |
| 5,119,811 | A | 6/1992 | Inglis et al. | |

(Continued)

FOREIGN PATENT DOCUMENTS

| | | | |
|---|---|---|---|
| DE | 691 07 376 | T2 | 6/1995 |
| DE | 691 31 486 | T2 | 2/2000 |

(Continued)

*Primary Examiner* — Douglas Y Sul
(74) *Attorney, Agent, or Firm* — Coloplast Corp., Coloplast A/S; Nick Baumann

(57) ABSTRACT

Reduction to the risk that artifacts occur in the cuff pressure measurement owing to accumulations of water in the cuff is by a tracheal ventilation device, including a cannula tube and an inflatable sleeve (cuff) arranged around the cannula tube. The sleeve is in fluid contact with a filling tube. In certain embodiments, the inner surface of the filling tube is formed by a solid hydrophilic layer. Further disclosed is a method that improves the pressure measurement in the sleeve of a conventional tracheal ventilation device.

14 Claims, 2 Drawing Sheets

(56) References Cited

U.S. PATENT DOCUMENTS

| | | | | | |
|---|---|---|---|---|---|
| 5,599,291 | A * | 2/1997 | Balbierz | A61L 31/10 604/8 |
| 5,913,249 | A * | 6/1999 | Weckstrom | A61B 5/087 73/861.52 |
| 6,165,166 | A * | 12/2000 | Samuelson | B29C 48/12 604/524 |
| 11,123,520 | B2 * | 9/2021 | Searle | A61M 25/0043 |
| 2004/0127598 | A1 | 7/2004 | McGhee | |
| 2008/0078406 | A1 | 4/2008 | Clayton et al. | |
| 2008/0092902 | A1 | 4/2008 | Schnell | |
| 2008/0215034 | A1 * | 9/2008 | Clayton | A61L 29/085 604/509 |
| 2008/0236593 | A1 * | 10/2008 | Nelson | A61M 16/04 128/207.15 |
| 2011/0027334 | A1 * | 2/2011 | Maguire | A61M 16/04 264/279.1 |
| 2014/0261443 | A1 * | 9/2014 | Lowenstein | A61M 16/044 128/207.15 |
| 2017/0043111 | A1 * | 2/2017 | Hoftman | A61M 16/0404 |
| 2017/0095629 | A1 * | 4/2017 | Bateman | A61M 16/0427 |

FOREIGN PATENT DOCUMENTS

| | | | |
|---|---|---|---|
| DE | 60 2004 004 557 | T2 | 10/2007 |
| EP | 1 861 152 | B1 | 9/2018 |
| WO | WO-92/11896 | A1 | 7/1992 |

* cited by examiner

TRACHEAL VENTILATION DEVICE HAVING OPTIMIZED CUFF TUBE

CROSS-REFERENCE TO RELATED APPLICATIONS

This application is a National Stage of International Application No. PCT/EP2021/053948 filed Feb. 18, 2021, which claims benefit of German Patent Application No. 10 2020 105 522.6 filed Mar. 2, 2020, each of which are herein incorporated in their entirety.

TECHNICAL FIELD

The present invention relates to a tracheal ventilation device, in particular an endotracheal tube or tracheostomy tube, wherein the tracheal ventilation device comprises a cannula tube and an inflatable sleeve disposed around the cannula tube, wherein the sleeve is in fluid contact with a filling hose. The invention in particular relates to devices and measures for improving pressure measurement in the sleeve of a tracheal ventilation device of the aforementioned type.

BACKGROUND

Many tracheal ventilation devices are equipped with an inflatable sleeve, the so-called cuff. This is essentially an inflatable sealing balloon that is located on the distal side just before the patient end of the tube. Air is introduced via a filling valve to fill the cuff. Said air enters the cuff via the filling hose and a hand-held manometer, for example, which has an inflation function and is provided for this purpose can be used to introduce the air.

The task of the cuff is to seal the air tube around the tube. On the one hand, for artificially ventilated patients, this sealing effect of the cuff ensures that the ventilation air provided by a ventilator enters the bronchi completely and from there also exits the patient again through the tube. If the cuff were not sealing sufficiently, significant amounts of ventilation air could escape through the natural airways. On the other hand, the seal provided by the cuff prevents secretions from the subglottic region from entering the bronchi, which could otherwise lead to aspiration-associated pneumonia.

Most tracheal ventilation devices of the type described here are equipped with so-called "high-volume, low-pressure (HVLP) cuffs". Unlike an expandable balloon, in HVLP cuffs the material of the cuff is not intended to expand upon inflation. The trachea is instead sealed by the inflated cuff having a significantly larger diameter (approx. 30%) when free than the provided air tube. In the intended application, the air-filled cuff conforms to the contours of the trachea, forming folds.

This type of cuff has the advantage that the measurable cuff pressure corresponds exactly to the pressure with which the cuff presses on the trachea. To ensure a sufficient seal despite the folds, a standard cuff should be filled with approximately 15-30 mbar. In order to achieve sufficient sealing even with the lowest possible cuff pressures, cuffs with the thinnest possible wall thickness are desired. On the other hand, to avoid tracheal damage, the cuff pressure should not be allowed to rise into the range of capillary perfusion pressure. The cuff pressure should therefore be set to no more than 30 mbar if possible.

For the reasons stated above, it is necessary to be able to set the cuff pressure very precisely in order to achieve the desired seal on the one hand and to avoid tracheal damage on the other. For this reason, it is customary to check the cuff pressure regularly (e.g., every 4 hours) or regulate it continuously using a suitable device.

It is not uncommon for condensation to accumulate inside the cuff. This is water that has diffused through the cuff wall into the interior of the cuff. This can become problematic during further use if water from the cuff enters the filling hose when the cuff pressure is checked or readjusted, or also when the cuff is intentionally relaxed temporarily. This can lead to the occurrence of artifacts when the cuff pressure is checked, because the water in the filling hose interferes with the connection between the measuring device and the cuff.

Artifacts can occur in particular when the water in the filling hose is interrupted by many small air bubbles. In these cases, the pressure set in the control balloon may not be sufficient to force the water in the filling hose into the cuff. This means that no air gets into the cuff and therefore no pressure is built up, even though a manometer connected to the control balloon indicates the desired pressure.

To reduce the risk of water formation in the cuffs, cuffs having thicker walls are sometimes used. However, cuffs with thick walls do not seal against aspiration as well as thin cuffs. The use of materials that have very good barrier properties to water, such as polypropylene, polyethylene, polyester or Teflon, could also be an option. These materials do not bond well, however, which is why most manufacturers of endotracheal tubes, tracheostomy tubes, and other tracheal ventilation devices comprising HVLP cuffs use PVC or polyurethane. The water barrier properties of polyurethane are quite unfavourable though, and water consequently accumulates very quickly, in particular in the case of thin polyurethane cuffs. The barrier properties of PVC are admittedly significantly better than those of polyurethane, but water has been observed in the cuff even in PVC cuffs having wall thicknesses of 90 μm.

To prevent the accumulation of condensation in the cuff, EP 1 861 152 B1 describes a cuff comprising a water-impermeable coating. Such a coating can reduce the flexibility of the cuff, however, and thus reduce its sealing performance against secretions.

The inner diameter of the filling hose could alternatively also be much larger than usual in order to ensure the free passage of gas when measuring the pressure in the cuff. However, the consequence of this would be that the wall thickness of the cannulas would have to be increased to accommodate the filling hose with its larger inner diameter, which would be at the expense of the cross-section of the lumen of the cannula tube.

SUMMARY

The object of the present invention is therefore to provide a new technical solution with which the risk of artifacts occurring in the cuff pressure measurement due to water accumulation in the cuff can be reduced.

This object is achieved according to the invention by a tracheal ventilation device comprising a cannula tube and an inflatable sleeve (cuff) disposed around the cannula tube, wherein the sleeve is in fluid contact with a filling hose, characterised in that the inner surface of the filling hose is formed by a solid hydrophilic layer.

The tracheal ventilation device claimed according to the invention is suitable for insertion into the trachea to enable breathing via said device. For this purpose, the tracheal ventilation device comprises a cannula tube which can be inserted into the air tube and the tube wall of which extends between the tube opening at the proximal end of the tube and the tube opening at the distal end of the tube and defines a lumen through which breathing air or breathing gas can flow when it is inserted in the trachea. In certain embodiments, the tracheal ventilation device is an endotracheal tube that is passed through the larynx into the trachea; in other embodiments, it is a tracheostomy tube that is also frequently referred to as a tracheostomy cannula. This tube is inserted into the trachea through a stoma in the neck.

In the context of the present invention, the terms "distal" and "proximal" are used from the perspective of a physician using the tracheal ventilation device, i.e., the proximal end of the tracheal ventilation device is the end which remains outside the body of the patient after insertion into the trachea, whereas the distal end of the tracheal ventilation device is inserted into the patient's trachea.

The inflatable sleeve on the outer wall of the cannula tube (cuff), which serves to seal the outer wall of the cannula tube against the inner wall of the air tube in a gas- and liquid-tight manner when inserted into the trachea, is preferably disposed as a ring around the cannula tube and is connected to the outer wall of the cannula tube at the contact surface in an all-around fluid-tight manner.

The filling hose is a hose the hose wall of which extends between the hose opening at the proximal end of the hose and the hose opening that opens into the inflatable sleeve at the distal end of the hose and defines a lumen through which air or other gas can be blown into the sleeve or air can be vented out of the sleeve when inserted into the trachea. The filling hose can be guided either in the tube wall of the cannula tube or along the inner wall or along the outer wall of the cannula tube.

The outer layer of the filling hose is made of an elastic hose material. This is typically an elastomer which can be selected from polyvinyl chloride, polyurethane, polyethylene, polypropylene, silicone, ethylene vinyl acetate copolymer, for example.

The hydrophilic layer proposed according to the invention is layered onto the inside of the outer hose layer of the filling hose and forms the boundary layer between the hose wall and the hose lumen. In some embodiments of the invention, the outer hose layer is comprised of more than one material, for example a first support layer disposed on the inner side of the outer filling hose layer and a second terminating or cover layer disposed on the outer side of the outer filling hose layer.

The term "layer" is understood here to mean a solid layer, i.e., a non-liquid layer. The hydrophilic layer proposed according to the invention covers the inner surface of the outer filling hose layer in a planar manner and is firmly connected to it.

In certain embodiments, a connecting layer can be provided between the outer hose layer and the inner hydrophilic layer as an adhesion promoter in order to achieve a particularly good connection between the outer hose layer and the inner hydrophilic layer.

Due to the firm connection between the hydrophilic layer and the inner surface of the outer filling hose layer, optionally via an interposed connecting layer (adhesion promoter), the hydrophilic layer cannot be dissolved and also not detached by water occurring in the filling hose, but remains firmly connected to the outer filling hose layer throughout the entire period of use of the tracheal ventilation device.

The term "hydrophilic" layer is in particular understood here to mean a layer consisting of a hydrophilic layer material, which, as measured using the sessile drop method and calculated using Young's equation $$\cos\Theta = \frac{\sigma SG - \sigma LS}{\sigma LG}$$

forms with distilled water at 20° C. a contact angle θ<80°. The contact angle is measured on a flat sample surface of the layer material used for the hydrophilic layer.

Certain embodiments of the invention are characterised in that the hydrophilic layer is composed of a material that forms a contact angle θ≤700 with water under the stated conditions. In special embodiments of the invention, the hydrophilic layer is composed of a material that forms a contact angle θ≤600 or even θ≤500 with water under the stated conditions.

The hydrophilic coating proposed according to the invention has the effect that water in the filling hose can already be moved in both directions even at pressure differences that are small relative to the intended cuff pressure. This ensures that the pressure between the manometer and the cuff is equalized. Tests carried out by the inventor of the present application have shown that the pressure difference necessary to force water through a filling hose can be reduced by up to a factor of 5 with the hydrophilic coating compared to a filling hose not equipped with a hydrophilic layer.

According to the invention, the hydrophilic layer is made of a material that forms a smaller contact angle θ with water under the stated conditions than the aforementioned conventional filling hose materials. In special embodiments of the invention, the hydrophilic layer is made of a material the contact angle θ of which is at least 15°, preferably at least 20°, even more preferably at least 250 smaller than the contact angle of the conventional filling hose material used for the outer hose layer.

In principle, the hydrophilic layer can be comprised of any hydrophilic material that is suitable for creating an inner coating in a filling hose and forms the required contact angle with water under the stated conditions. Examples of hydrophilic materials suitable for this purpose are selected from hydrophilic poly(lactams), polyurethanes, polyvinyl alcohol, polyvinyl ethers, maleic anhydride-based copolymers, vinylamines, polyethylenimines, polyethylene oxides, polypropylene oxides, poly(carboxylic acids), polyanhydrides, polyphosphazenes, polypeptides, polysaccharides and oligonucleotides which form the required contact angle with water under the stated conditions.

In certain embodiments, the hydrophilic material used to create the hydrophilic coating is selected from polyvinylpyrrolidone, polyvinylpyrrolidone copolymer, polyvinylpolypyrrolidone, polylactides, polyglycolides, and polycaprolactones that form the required contact angle with water under the stated conditions.

In special embodiments, the hydrophilic material used to create the hydrophilic coating is selected from celluloses, such as methyl cellulose, carboxymethyl cellulose, hydroxymethyl cellulose and hydroxypropyl cellulose or from salep mannan, guar gum, carobine, starch, xanthan gum, carmellose, hypromellose, macrogols, gum arabic, traganth, karaya gum, collagen, fibrin, elastin, chitosan, hyaluronic acid, alginates, gelatins, chitin, heparin and dextran pectin, carrageenan, agar and agarose.

In special embodiments, the hydrophilic layer is made of a hydrophilic polymer material which is selected from hydrophilic homo- and copolymers of acrylic acid, salts of homo- and copolymers of methacrylic acid, salts of homo- and copolymers of maleic acid, salts of homo- and copolymers of fumaric acid, salts of homo- and copolymers of monomers comprising sulphonic acid groups, homo- and copolymers of monomers comprising quaternary ammonium salts and mixtures and/or derivatives thereof, with the proviso that said materials form the contact angle with water required under the stated conditions.

The weight-average molecular weight MW of the aforementioned polymers is preferably in the range from 8,000 to 5,000,000 g/mol, preferably in the range from 20,000 to 3,000,000 g/mol, and even more preferably in the range from 200,000 to 2,000,000 g/mol. In certain embodiments, the polymer chains of respective polymer used are cross-linked with one another.

Expediently, the hydrophilic layer, like the material of the outer hose layer, is elastic. The hydrophilic layer is preferably made of an elastomer.

In certain embodiments, the hydrophilic layer is additionally characterised in that it is made of a water-swellable material. The swellable material is preferably a material capable of absorbing at least 1 g of distilled water per 1 g of swellable material at 20° C. In certain embodiments of the invention, the swellable material of the hydrophilic layer can absorb at least 10 g of distilled water or even at least 100 g of distilled water.

In the embodiments in which the hydrophilic layer is made of a water-swellable material, this material is preferably selected from materials which form a contact angle $\theta<30°$ with water in the swollen state under the stated conditions. In special embodiments of the invention, the hydrophilic layer is made of a material that forms a contact angle $\theta<25°$ or even $\theta<15°$ with water in the swollen state under the stated conditions.

To determine the contact angle of a layer material in the swollen state, the material is wetted with distilled water for 2 minutes before measuring the contact angle and any water remaining on the surface is then blown off with compressed air (6 bar, 1 second) immediately prior to the measuring the contact angle.

According to the invention, the hydrophilic layer is made of a material that forms a smaller contact angle θ with water in the swollen state under the stated conditions than the aforementioned conventional filling hose materials. In special embodiments of the invention, the hydrophilic layer is made of a material the contact angle θ of which in the swollen state is at least 15°, preferably at least 20°, even more preferably at least 250 smaller than the contact angle of the conventional filling hose material used for the outer hose layer.

To keep the cross-section of the lumen of the filling hose as large as possible, the layer thickness of the hydrophilic layer should be as small as possible. The layer thickness of the hydrophilic layer in the filling hose in the dry, i.e., not swollen, state is preferably in the range from 0.1 to 5 μm, wherein the dry state is understood here to be the state after 72 hours at 20° C. without contact with liquid water. In certain embodiments of the invention, the layer thickness of the hydrophilic layer in the dry state is in the range from 0.3 to 3 μm.

The thickness of the coating in the water-swollen state is preferably in the range from 10 to 200 μm. The thickness of the coating in the water-swollen state is preferably less than 150 μm, even more preferably less than 100 μm, and particularly preferably less than 50 μm. To determine the thickness of the coating in the swollen state, the material is wetted with distilled water for 2 minutes before measurement and any water remaining on the surface is then blown off with compressed air (6 bar, 1 second) immediately prior to measurement.

In the embodiments in which a connecting layer is provided as an adhesion promoter between the outer filling hose layer and the inner hydrophilic layer, the thickness of this connecting layer is preferably in the range from 10 nm to 10 μm. The thickness of the connecting layer in the water-swollen state is preferably less than 75 μm, even more preferably less than 50 μm, and particularly preferably less than 20 μm.

In certain embodiments, the tracheal ventilation device of the invention is characterised in that the filling hose provided on the inner side with a hydrophilic layer has an inner diameter of less than 1.2 mm in cross-section in the dry state. In special embodiments, the inner diameter of the filling hose in the dry state can even be less than or equal to 0.8 mm, or even less than or equal to 0.6 mm.

In certain embodiments, the tracheal ventilation device of the invention is characterised in that the filling hose provided on the inner side with a hydrophilic layer has an inner diameter of greater than or equal to 0.3 mm in cross-section in the swollen state.

In order to be able to check whether the cuff is inflated, in certain embodiments of the invention a control balloon that is in fluid contact with the lumen of the cuff is connected to the filling hose. The pressure can be roughly estimated by touching the control balloon. A limp control balloon already visually provides an indication that there is no increased pressure. A fully filled control balloon, on the other hand, visually indicates that there is increased pressure.

In certain embodiments of the invention, a filling valve is connected to the proximal end of the filling hose or to the proximal end of the control balloon via which air or another gas can be fed into the cuff through the filling hose.

In order to be able to measure the pressure in the cuff, a pressure measuring device can be connected to the filling hose, or to a control balloon provided on it, via the filling valve or another suitable connection. In certain embodiments, a suitably assembled manometer is connected to the control balloon or the filling hose to set and check the cuff pressure.

Depending on the specific embodiment, a suitable connector for connection to a breathing system is provided on the tracheal ventilation device and/or a neck plate as a contact surface on the patient's neck.

The present invention also includes a method for improving the pressure measurement in the sleeve of a conventional tracheal ventilation device, wherein the tracheal ventilation device comprises a cannula tube and an inflatable sleeve disposed around the cannula tube and wherein the sleeve is in fluid contact with a filling hose. According to the invention, the application of a hydrophilic layer to the inner wall of the filling hose is proposed to reduce the flow resistance.

In certain embodiments, the hydrophilic layer is applied to the inner wall of the filling hose directly during production of the tracheal ventilation device. In other embodiments, the hydrophilic layer is applied to the inner wall of the filling hose not until a later time after production of the tracheal ventilation device and preferably shortly prior to its use.

The hydrophilic layer is preferably applied by introducing the hydrophilic coating material that is intended to form the hydrophilic layer in a flowable form into the lumen of the conventional filling hose, which corresponds to the later outer hose layer. In different embodiments of the invention, the hydrophilic coating material is introduced into the filling hose either as a liquid material, as a suspension, as a solution or in the form of a foam or powder.

The conversion of the coating material introduced in liquid form, in dissolved form, in suspended form or in powder form into the not yet coated filling hose into a solid, insoluble layer that is firmly connected to the inner wall of the original filling hose is effected either by spontaneous curing, by drying, by using elevated temperature or by irradiation with light. In certain embodiments, this leads to polymerization of the coating material, crosslinking of the coating material and/or chemical bonding of the coating material to the material of the inner surface of the filling hose (grafting) or a connecting layer provided upon it.

Example of Embodiment

A filling hose made of PVC and having an inner diameter of 0.7 mm was filled with polyvinylpyrrolidone and heated for 30 minutes to 80° C. The thickness of the resulting hydrophilic coating was 3 km.

The hydrophilic coating led to the water in the filling hose being able to be moved through the filling hose even at very small pressure differences. In one test, it was possible to reduce the pressure difference required to force the water through the filling hose from 75 mbar to 15 mbar.

BRIEF DESCRIPTION OF THE FIGURES

Further advantages, features, and possible applications of the present invention will become apparent from the following description of an embodiment and the associated figures, whereby the same reference signs refer to the same elements. The figures show.

DETAILED DESCRIPTION OF PARTICULAR EMBODIMENTS

Figure 1:
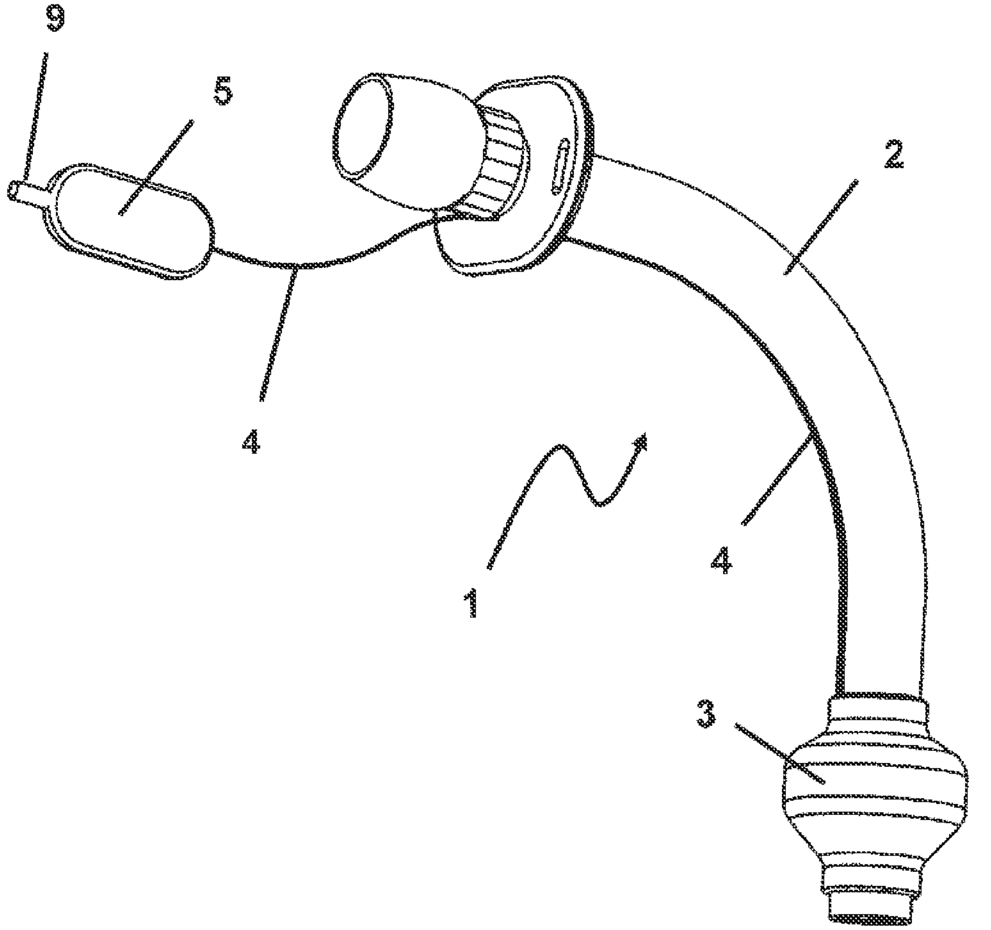
FIG. 1: a tracheal ventilation device according to one embodiment of the present invention.

FIG. 1 shows a tracheal ventilation device according to one embodiment of the present invention. The tracheal ventilation device 1 shown here is a tracheostomy cannula comprising a cannula tube 2 and a sleeve (cuff) 3 that is tightly connected to the outside of the cannula tube 2. The cuff 3 is connected to a control balloon 5 in fluid communication via a filling hose 4. The cuff 3 can be filled with a gas via the filling hose 4 or the cuff pressure can be regulated via the filling valve 9 on the control balloon 5.

Figure 2:
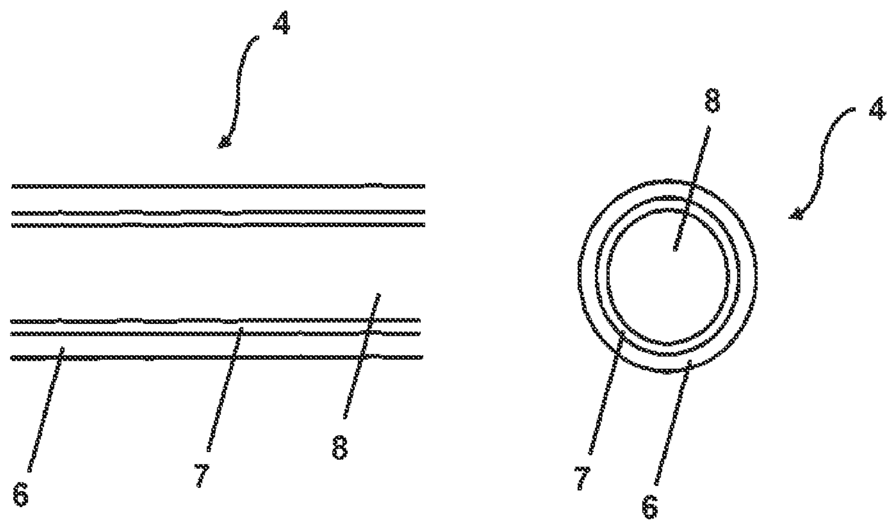
FIG. 2: both a longitudinal section and a cross-section through the filling hose of the tracheal ventilation device of FIG. 1.

As schematically shown in FIG. 2, which shows an enlarged longitudinal section through the filling hose 4 on the left side and an enlarged cross-section through the filling hose 4 on the right side, the inner surface of the filling hose 4 is formed by a hydrophilic layer 7 provided on the inner side of the outer hose layer 6 made of conventional hose material. The hydrophilic layer 7 rests on the inner side of the outer hose layer 6 and is firmly, i.e., insolubly, connected to it. To the inside, the surface of the hydrophilic layer 7 defines the hose lumen 8.

For the purpose of the original disclosure, it should be noted that all of the features as they become apparent to a person skilled in the art from the present description, the drawings and the claims, even if they have been specifically described only in connection with specific other features, can be combined both individually and in any combination with other features or groups of features disclosed here, insofar as this has not been expressly excluded or technical circumstances make such combinations impossible or pointless. A comprehensive, explicit presentation of all conceivable combinations of features is omitted here solely for the sake of brevity and legibility of the description.

Although the invention has been presented and described in detail in the drawings and the foregoing description, this representation and description is merely an example and is not intended to limit the scope of protection as defined by the claims. The invention is not limited to the disclosed embodiments.

Modifications of the disclosed embodiments will be obvious to those skilled in the art from the drawings, the description and the appended claims. In the claims, the word "comprise" does not exclude other elements or steps, and the indefinite article "a" does not exclude a plurality. The mere fact that certain features are claimed in different claims does not preclude their combination. Reference signs in the claims are not intended to limit the scope of protection.

LIST OF REFERENCE SIGNS

1 Tracheal ventilation device
2 Cannula tube
3 Sleeve (cuff)
4 Filling hose
Control balloon
6 Outer hose layer
7 Hydrophilic layer
8 Hose lumen
9 Filling valve

The invention claimed is:

1. A tracheal ventilation device comprising:
a cannula tube;
a filling hose having an inner diameter; and
an inflatable sleeve disposed around the cannula tube and in fluid contact with the filling hose,
wherein an inner surface of the filling hose comprises a hydrophilic layer of water-swellable material that is transitionable between a dry state ranging from 0.1 to 5 μm in layer thickness and a water-swollen state ranging from 10 to 200 μm in layer thickness, and
wherein transitioning of the hydrophilic layer of water-swellable material from the dry state to the water-swollen state causes a reduction of the inner diameter of the filling hose.

2. The tracheal ventilation device according to claim 1, wherein when measured using a sessile drop method and calculated using Young's equation with distilled water at 20° C., the hydrophilic layer of water-swellable material forms a contact angle $\theta<80°$.

3. The tracheal ventilation device according to claim 1, wherein the hydrophilic layer covers the inner surface of an outer filling hose layer in a planar manner and is firmly connected to the inner surface.

4. The tracheal ventilation device according to claim 1, wherein the hydrophilic layer is made of a hydrophilic polymer material which is selected from hydrophilic poly (lactams), polyurethanes, polyvinyl alcohol, polyvinyl ethers, maleic anhydride-based copolymers, polyesters, vinylamines, polyethylenimines, polyethylene oxides, polypropylene oxides, poly(carboxylic acids), polyamides, polyanhydrides, polyphosphazenes, polypeptides, polysaccharides, polyesters, oligonucleotides, polyvinylpyrrolidone, polyvinylpyrrolidone copolymer, polyvinylpolypyrrolidone, polylactides, polyglycolides and polycaprolactones.

5. The tracheal ventilation device according to claim 1, wherein the hydrophilic layer is made of a hydrophilic polymer material which is selected from hydrophilic homo- and copolymers of acrylic acid, salts of homo- and copolymers of methacrylic acid, salts of homo- and copolymers of maleic acid, salts of homo- and copolymers of fumaric acid, salts of homo- and copolymers of monomers comprising sulphonic acid groups, homo- and copolymers of monomers comprising quaternary ammonium salts and mixtures and/or derivatives thereof.

6. The tracheal ventilation device according to claim 1, wherein, when the water-swellable material is in the dry state, the inner diameter of the filling hose is less than 1.0 mm.

7. The tracheal ventilation device according to claim 1, wherein, when the water-swellable material is in the water-swollen state, the inner diameter of the filling hose is more than 0.3 mm.

8. A method for improving pressure measurement in an inflatable sleeve of a tracheal ventilation device via a filling hose, wherein the tracheal ventilation device comprises a cannula tube and the inflatable sleeve disposed around the cannula tube, wherein the inflatable sleeve is in fluid contact with the filling hose, the method comprising:

applying a hydrophilic layer to the filling hose such that an inner wall of the filling hose that defines an inner diameter of the filling hose, the inner wall comprising is a hydrophilic layer of water-swellable material that is transitionable between a dry state ranging from 0.1 to 5 μm in layer thickness and a water-swollen state ranging from 10 to 200 μm in layer thickness, wherein transitioning from the dry state to the water-swollen state causes a reduction of the inner diameter.

9. The method according to claim 8, wherein the hydrophilic layer is applied to the inner wall of the filling hose directly during production of the tracheal ventilation device or not until a later time after production of the tracheal ventilation device and prior to its use.

10. The method according to claim 8, wherein the hydrophilic layer is applied by introducing a hydrophilic coating material in a flowable form into a lumen of the filling hose.

11. The method according to claim 10, wherein the hydrophilic coating material is introduced into the filling hose in liquid form, in dissolved form, in suspended form or in powder form.

12. The method according to claim 10, wherein the hydrophilic coating material introduced into the filling hose is converted into a solid coating on the inner wall of the filling hose by spontaneous curing, by drying, by using elevated temperature, and/or by irradiation with light.

13. A tracheal ventilation device comprising:

a cannula tube;

a filling hose comprising:

an outer filling hose layer having a first inner diameter of less than 1.0 mm, and a solid hydrophilic layer provided on an inner side of the outer filling hose layer, the solid hydrophilic layer defining an inner surface of the filling hose, wherein a second inner diameter defined by the solid hydrophilic layer is less than the first inner diameter of the outer filling hose layer, and the solid hydrophilic layer is transitionable between a dry state having a dry-state layer thickness and a water-swollen state having a water-swollen layer thickness that is at least 40 times the dry-state layer thickness, such that transitioning from the dry state to the water-swollen state causes a reduction of the second inner diameter of the filling hose; and an inflatable sleeve in fluid contact with the filling hose and disposed around the cannula tube.

14. The tracheal ventilation device according to claim 13, the filling hose further comprising:

a connecting layer provided between the outer filling hose layer and the solid hydrophilic layer, the connecting layer having a layer thickness in a range from 10 nm to 10 μm.

* * * * *